United States Patent
Inoue et al.

(10) Patent No.: US 10,307,062 B2
(45) Date of Patent: Jun. 4, 2019

(54) HOLDER AND LIGHT MEASURING DEVICE USING SAME

(75) Inventors: Yoshihiro Inoue, Kyoto (JP); Takashi Amita, Kyoto (JP); Satoru Kohno, Tokyo (JP); Akihiro Ishikawa, Kyoto (JP); Yoshinori Masuda, Kyoto (JP); Haruhide Udagawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 334 days.

(21) Appl. No.: 13/635,501

(22) PCT Filed: Mar. 18, 2010

(86) PCT No.: PCT/JP2010/054628
§ 371 (c)(1),
(2), (4) Date: Nov. 27, 2012

(87) PCT Pub. No.: WO2011/114479
PCT Pub. Date: Sep. 22, 2011

(65) Prior Publication Data
US 2013/0066214 A1    Mar. 14, 2013

(51) Int. Cl.
*A61B 5/00*    (2006.01)
*A61B 6/00*    (2006.01)

(52) U.S. Cl.
CPC .......... *A61B 5/0059* (2013.01); *A61B 5/0042* (2013.01); *A61B 5/6814* (2013.01);
(Continued)

(58) Field of Classification Search
CPC ............ A61B 5/05; A61B 6/00; A61B 5/0059
(Continued)

(56) References Cited

U.S. PATENT DOCUMENTS 2,426,958 A * 9/1947 Ulett, Jr. et al. .............. 600/383
3,998,213 A * 12/1976 Price .............................. 600/383
(Continued)

FOREIGN PATENT DOCUMENTS

JP    2001-137217 A    5/2001
JP    2001-286449 A    10/2001
(Continued)

OTHER PUBLICATIONS

G. Strangman, Factors affecting the accuracy of near-infrared spectroscopy concentration calculations for focal changes in oxygenation parameters, NeuroImage, 18 (2003) pp. 865-879.

*Primary Examiner* — Tse W Chen
*Assistant Examiner* — Patrick M Mehl
(74) *Attorney, Agent, or Firm* — McDermott Will & Emery LLP

(57) ABSTRACT

Provided is a holder which comprises at least two probe mount portions and is to be put on the head of a subject by inserting a light-transmitting probe for emitting light from the tip thereof or a light-receiving probe for receiving light through the tip thereof in the probe mount portion, the holder characterized by being provided with a linear backbone portion extending in a first direction, at least two linear branch portions extending in a second direction different from the first direction, and a disposition reference point disposed so as to match a first specific point, the first specific point being set in the head of the subject.

6 Claims, 12 Drawing Sheets

(52) U.S. Cl.
CPC ..... *A61B 5/4064* (2013.01); *A61B 2562/0233* (2013.01); *A61B 2562/046* (2013.01)

(58) Field of Classification Search
USPC ........................................ 600/476, 407, 473
See application file for complete search history.

(56) References Cited

U.S. PATENT DOCUMENTS

| | | | |
|---|---|---|---|
| 6,510,340 B1* | 1/2003 | Jordan | 600/544 |
| 2003/0009104 A1* | 1/2003 | Hyman et al. | 600/476 |
| 2004/0127784 A1* | 7/2004 | Yamashita et al. | 600/407 |
| 2007/0238945 A1* | 10/2007 | Delic et al. | 600/383 |
| 2008/0269848 A1* | 10/2008 | Birmingham et al. | 607/89 |

FOREIGN PATENT DOCUMENTS

| | | |
|---|---|---|
| JP | 2001-337033 A | 12/2001 |
| JP | 2007-236963 A | 9/2007 |
| JP | 2007-315827 A | 12/2007 |
| JP | 2008-67904 A | 3/2008 |
| JP | 2009-77841 A | 4/2009 |
| JP | 2009-261588 A | 11/2009 |

* cited by examiner (a)

(b)

(a)

(b)

(a)

(b)

(a)

(b)

(a)

(b)

HOLDER AND LIGHT MEASURING DEVICE USING SAME

CROSS REFERENCE TO PRIOR APPLICATIONS

This application is a U.S. National Phase application under 35 U.S.C. § 371 of International Application No. PCT/JP2010/054628, filed on Mar. 18, 2010. The International Application was published in Japanese on Sep. 22, 2011 as WO 2011/114479 A1 under PCT Article 21(2). All of the applications are herein incorporated by reference.

TECHNICAL FIELD

The present invention relates to a holder and a light measuring device using the same, and in particular to a holder having a number of light transmitting points for illuminating a living body with light and a number of light receiving points for receiving light emitted from the living body, and for measuring information on the inside of a living body for a number of channels which are set for each pair of one light transmitting point and one light receiving point, and a light measuring device using the same.

BACKGROUND ART

In recent years, optical brain function imaging devices (light measuring devices) for a simple noninvasive measurement using light have been developed in order to observe brain activity. In such an optical brain function imaging device, the brain is irradiated with near infrared rays having three different wavelengths $\lambda_1$, $\lambda_2$ and $\lambda_3$ (780 nm, 805 nm and 830 nm, for example) from the light-transmitting probes placed on the surface of the head of the subject, and at the same time, the intensity $A(\lambda_1)$, $A(\lambda_2)$ and $A(\lambda_3)$ (information on the amount of received light) of the near infrared rays of each wavelength $\lambda_1$, $\lambda_2$ and $\lambda_3$ released from the brain is respectively detected by the light-receiving probes placed on the surface of the head.

In order to find the product [oxyHb] of the concentration of oxyhemoglobin in the cerebral blood flow and the length of the light path and the product [deoxyHb] of the concentration of deoxyhemoglobin in the cerebral blood flow and the length of the light path from the thus-gained information on the amount of received light $A(\lambda_1)$, $A(\lambda_2)$ and $A(\lambda_3)$, the Modified Beer-Lambert Law has been used to prepare simultaneous equations shown in the relational expressions (1), (2) and (3), for example, and these simultaneous equations have been solved (see Non-Patent Document 1). Furthermore, the product ([oxyHb]+[deoxyHb]) of the concentration of total hemoglobin and the length of the light path has been calculated from the product [oxyHb] of the concentration of oxyhemoglobin and the length of the light path and the product [deoxyHb] of the concentration of deoxyhemoglobin and the length of the light path.

$$A(\lambda_1)=E_O(\lambda_1)\times[oxyHb]+E_d(\lambda_1)\times[deoxyHb] \quad (1)$$

$$A(\lambda_2)=E_O(\lambda_2)\times[oxyHb]+E_d(\lambda_2)\times[deoxyHb] \quad (2)$$

$$A(\lambda_2)=E_O(\lambda_3)\times[oxyHb]+E_d(\lambda_3)\times[deoxyHb] \quad (3)$$

Here, $E_O(\lambda m)$ is the coefficient of absorbance of the oxyhemoglobin for the light of the wavelength $\lambda m$, and $E_d(\lambda m)$ is the coefficient of absorbance of the deoxyhemoglobin for the light of the wavelength $\lambda m$.

Here, the relationship between the distance between a light-transmitting probe and a light-receiving probe (channel) and the portion to be measured is described. FIG. 7(a) is a cross-sectional diagram showing the relationship between a pair of probes, a light-transmitting probe and a light-receiving probe, and the portion to be measured, and FIG. 7(b) is a plan diagram of FIG. 7(a).

A light-transmitting probe 12 is pressed against a light transmitting point T on the surface of the head of a subject, and at the same time, a light-receiving probe 13 is pressed against a light receiving point R on the surface of the head of the subject. Thus, light is emitted from the light-transmitting probe 12, and at the same time, the light released from the surface of the head enters into the light-receiving probe 13. At this time, the light that has passed through the banana-shaped area (area to be measured) from among the light emitted from the light transmitting point T on the surface of the head reaches the light receiving point R on the surface of the head. As a result, information on the amount of received light $A(\lambda_1)$, $A(\lambda_2)$ and $A(\lambda_3)$ concerning the portion to be measured S of the subject at a depth L/2, which is half of the distance along the line connecting the light transmitting point T and the light receiving point R along the surface of the head of the subject from the mid-point M of the line L connecting the light transmitting point T and the light receiving point R along the surface of the head of the subject, is particularly gained from among the area to be measured.

In optical brain function imaging devices, a near infrared spectrometer, for example, is used in order to measure the product [oxyHb] of the concentration of oxyhemoglobin and the length of the light path, the product [deoxyHb] of the concentration of deoxyhemoglobin and the length of the light path, and the product ([oxyHb]+[deoxyHb]) of the concentration of total hemoglobin and the length of the light path concerning a number of portions to be measured in the brain (see Patent Document 1).

FIG. 8 is a block diagram schematically showing an example of the structure of a conventional near infrared spectrometer. Here, several optical fibers for transmitting light and several optical fibers for receiving light are omitted in order to simplify the drawing.

A near infrared spectrometer 201 has a housing 11 in a rectangular parallelepiped form (70 cm×100 cm×120 cm, for example).

A light source 2 for emitting light, a light source driving mechanism 4 for driving the light source 2, a light detector 3 for detecting light, an A/D converter 5, a control unit 21 for transmitting and receiving light, a control unit 22 for analysis and a memory 23 are provided inside the housing 11, and at the same time, 64 light-transmitting probes (light-transmitting means) 12, 64 light-receiving probes (light-receiving means) 13, 64 optical fibers 14 for transmitting light, 64 optical fibers 15 for receiving light, a display 26 having a monitor screen 26a, and a keyboard (input device) 27 are provided outside the housing 11.

The light source driving mechanism 4 drives the light source 2 using a drive signal inputted from the control unit 21 for transmitting and receiving light. The light source 2 is made of semiconductor lasers LD1, LD2, LD3 and the like that can emit near infrared rays having three different wavelengths $\lambda_1$, $\lambda_2$ and $\lambda_3$, for example.

The light detector 3 is a detector for outputting a light reception signal (information on the amount of received light) $A(\lambda_1)$, $A(\lambda_2)$ or $A(\lambda_3)$ to the control unit 21 for transmitting and receiving light via the A/D converter 5 by detecting the respective near infrared rays and is a photomultiplier, for example.

The optical fibers 14 for transmitting light and the optical fibers 15 for receiving light are tubular with a diameter of 2 mm and a length of 2 meters to 10 meters and can convey near infrared rays in the direction of the axis so that the near infrared rays that have entered through one end pass through the inside so as to emit through the other end.

One optical fiber 14 for transmitting light is connected to one probe 12 for transmitting light and one semiconductor laser LD1, LD2 or LD3 in the light source 2 at the two ends so that the two are away from each other at a set length (2 meters to 10 meters).

One optical fiber 15 for receiving light is connected to one probe 13 for receiving light and one photomultiplier in the light detector 3 at the two ends so that the two are away from each other at a set length (2 meters to 10 meters).

In this near infrared spectrometer 201, a holder 30 is used in order to make the 64 light-transmitting probes 12 and the 84 light-receiving probes 13 make contact with the surface of the head of a subject in a predetermined alignment. FIG. 9 is a plan diagram showing an example of the holder 30 into which 64 light-transmitting probes and 64 light-receiving probes are inserted.

The light-transmitting probes $12_{T1}$ to $12_{T64}$ and the light-receiving probes $13_{R1}$ to $13_{R64}$ are aligned alternately in a matrix of 16 in the longitudinal direction and 16 in the lateral direction. As a result, the distance between the light-transmitting probes 12 and the light-receiving probes 13 is constant so that the information on the amount of received light A ($\lambda_1$), A ($\lambda_2$) and A ($\lambda_3$) is gained at a certain depth from the surface of the head. Here, a channel of 30 mm is generally used, and in the case where the channel is 30 mm, it is possible for the information on the amount of received light A ($\lambda_1$), A ($\lambda_2$) and A ($\lambda_3$) to be gained at a depth of 15 mm to 20 mm from the mid-point of each channel. That is to say, the locations at a depth of 15 mm to 20 mm from the surface of the head approximately correspond to the portions on the surface of the brain, and thus, the amount of received light A ($\lambda_1$), A ($\lambda_2$) and A ($\lambda_3$) concerning the brain activity is gained.

The curvature of the surface of the head differs depending on the sex, the age and the individual, and therefore, a holder that can be easily worn on the head with a different curvature of the surface has been proposed. In the holder, support portions for holding the light-transmitting probes 12 and the light-receiving probes 13 are aligned in a tetragonal lattice on the surface of the head, and the support portions are linked at a set distance (30 mm, for example) with connection portions that do not exhibit stretchability, and furthermore, the connection portions are rotatable by a predetermined angle or less with the support portions as a rotational axis in a plane through which the holder makes contact with the surface of the head (see Patent Document 2).

This holder 30 is provided with 128 socket parts 33 for fixing the light-transmitting probes 12 and the light-receiving probes 13, 480 connection parts 31 and 128 nut parts 32.

Here, FIG. 10 is an exploded perspective diagram showing a light-transmitting probe 12, a nut part 32, two connection parts 31 and a socket part 33, and FIG. 11 is a diagram showing the light-transmitting probe 12, the nut part 32, the two connection parts 31 and the socket part 33 after assembly.

The connection parts 31 are plates in an I-shape. In addition, the connection parts 31 have insertion portions 31a in annular form at the two ends and a linking portion 31b for linking the insertion portions 31a at the two ends at a set distance. Circular through holes through which a socket part 33 is inserted are created at the center of the respective insertion portions 31a. In addition, the linking portion 31b has a width of 10 mm and a thickness of 0.1 mm with a set distance of 31.5 mm, which is the distance between the centers of the through holes at the two ends. The linking portion 31 is formed so as to have flexibility only in the direction of the thickness. That is to say, the insertion portions 31a at the two ends are always held at a channel length X.

The socket part 33 has a main body portion 33a in cylindrical form, a flange 33b in annular form and a bottom 33c in annular form so that a light-transmitting probe 12 or a light-receiving probe 13 can be inserted inside, and at the same time, the outside of the main body portion 33a is threaded so that the nut part 32 can be engaged.

The nut part 32 is in annular shape having a circular through hole, and the inside is threaded so that the main body portion 33a of the socket part 33 can be engaged. Here, the size of the through hole is greater than that of the main body portion 33a of the socket part 33 and is smaller than that of the flange 33b of the socket part 33 as viewed from the top.

As a result, the insertion portion 31a of a connection part 31 can be sandwiched between the flange 33b of the socket part 33 and the nut part 32 so as to be fixed when the main body portion 33a of the socket part 33 is screwed into the nut part 32. Here, the insertion portion 31a of one connection part 31 is sandwiched between the flange 33b of the socket part 33 and the nut part 32 when one connection part 31 is fixed. Meanwhile, the insertion portions 31a of four connection parts 31 are sandwiched between the flange 33b of the socket part 33 and the nut part 32 when four connection parts 31 are fixed. That is to say, any number of connection parts 31 can be fixed.

The light-transmitting probes 12 are in cylindrical form (diameter: 5 mm, for example), which can fix a socket part 33. An optical fiber 14 for transmitting light (diameter: 1 mm, for example) that is connected to the light source 2 is fixed to the inside of a light-transmitting probe 12 with a spring in between so that light can be emitted from the end of the optical fiber 14 for transmitting light.

In addition, the light-receiving probes 13 have the same structure as the light-transmitting probes 12 and are in cylindrical form (diameter: 5 mm, for example), which can fix a socket part 33. Thus, an optical fiber 15 for receiving light (diameter: 1 mm, for example) that is connected to the light detector 3 is fixed to the inside of a light-receiving probe 13 with a spring in between so that light can be received by the end of the optical fiber 15 for receiving light.

A holder 30, as in FIG. 9, is made of 128 socket parts 33, 480 connection parts 31 and 128 nut parts 32, for example. A doctor or another person who carries out the measurement slightly loosens the screw mechanism between the flange 33b of a socket part 33 and a nut part 32 so that one connection part 31 and another connection part 31 are fixed to each other by forming a desired angle around the socket part 33 as viewed from above, as shown in FIG. 11(a), and at the same time, the linking portion 31b of the connection part 31 can deform due to its flexibility, as shown in FIG. 11(b), so as to have a curvature that matches the surface of the head, and thus, this holder 30 can make close contact with the surface of the head when being worn. The doctor or the other person firmly fixes the screw mechanism between the flange 33b of the socket part 33 and the nut part 32 in the thus-deformed state. Then, the holder 30 does not return to a flat state, and as a result, the curvature is maintained. Finally, the doctor or the other person inserts the light-transmitting probes 12 and the light-receiving probes 13 into the socket parts 33 in a predetermined alignment.

In the positional relationship between these 64 light-transmitting probes 12T1 to 12T64 and 64 light-receiving probes 13R1 to 13R64, it is necessary to adjust the timing in the emissions of light from the light-transmitting probes 12 and the receptions of light by the light-receiving probes 13 so that one light-receiving probe 13 receives light emitted from only one light-transmitting probe 12 instead of receiving light emitted from a number of light-transmitting probes 12 simultaneously. Therefore, the memory 23 stores a control table showing the timing according to which the light source 2 emits light and the light detector 3 detects the light.

The control unit 21 for transmitting and receiving light where this control table is stored in the memory 23 outputs a drive signal for allowing one light-transmitting probe 12 to transmit light to the light source driving mechanism 4, and at the same time allows the light detector 3 to detect the light reception signal (information on the amount of received light) received by the light-receiving probe 13.

As a result, as shown in FIG. 9 as a plan view, a total of 480 pieces (S1 to S480) of information on the amount of received light A ($\lambda$1), A ($\lambda$2) and A ($\lambda$3) is collected.

Thus, the control unit 22 for analysis finds the product [oxyHb] of the concentration of oxyhemoglobin and the length of the light path, the product [deoxyHb] of the concentration of deoxyhemoglobin and the length of the light path, and the product ([oxyHb]+[deoxyHb]) of the concentration of total hemoglobin and the length of the light path from the intensity of the light that has passed of each wavelength (wavelength of light absorbed by oxyhemoglobin and the wavelength of light absorbed by deoxyhemoglobin) by using the relational expressions (1), (2) and (3) on the basis of the total of the 232 pieces of information on the amount of received light A ($\lambda$1), A ($\lambda$2) and A ($\lambda$3).

PRIOR ART DOCUMENTS

Patent Documents

Patent Document 1: Japanese Unexamined Patent Publication 2001-337033
Patent Document 2: Japanese Unexamined Patent Publication 2009-077841.

Non Patent Document

Non-Patent Document 1: Factors affecting the accuracy of near-infrared spectroscopy concentration calculations for focal changes in oxygenation parameters, NeuroImage 18, 865-879, 2003.

SUMMARY OF THE INVENTION

Problem to be Solved by the Invention

In order for the above-described holder 30 to be made to make close contact with the surface of the head of a subject, a doctor or another person needs to change the form of the holder 30 so that the surface thereof has such a curvature as to match the surface of the head by adjusting the angle to a desired angle between one connection part 31 and another connection part 31 around a socket part 33 as the rotational axis, and then firmly secure the screw mechanism between the flange 33b and the nut part 32 of the socket part 33.

Accordingly, in the case where the above-described holder 30 is made to make close contact with the surface of the head of a subject, the screw mechanisms between the flanges 33b and the nut parts 32 of a great number (128) of socket parts 33 must be firmly fixed, which is very troublesome for the doctor or the other person and is very stressful for the subject because he or she needs to keep still for a long period of time.

Furthermore, light-transmitting probes $12_{T1}$ to $12_{T64}$ and light-receiving probes $13_{R1}$ to $13_{R64}$ are attached to the holder 30 after the holder 30 is made to make close contact with the surface of the head of a subject. There is hair on the surface of the head of a human body, and therefore, the ends of the light-transmitting probes $12_{T1}$ to $12_{T64}$ and the light-receiving probes $13_{R1}$ to $13_{R64}$ must be made to make contact with the surface of the head while avoiding the hair, which makes it necessary to push the hair aside when attaching the light-transmitting probes $12_{T1}$ to $12_{T64}$ and the light-receiving probes $13_{R1}$ to $13_{R64}$.

Therefore, when the light-transmitting probes $12_{T1}$ to $12_{T64}$ and the light-receiving probes $13_{R1}$ to $13_{R64}$ are attached to the holder 30, the hair must be pushed aside, which is very troublesome for the doctor or the other person and is very stressful for the subject because he or she needs to keep still for a long period of time.

In the case where a change in the blood flow through the portions within the brain of a subject as time elapses is measured when the subject is exercising, such as for rehabilitation, it is not necessary to collect information on the amount of received light A ($\lambda$1), A ($\lambda$2) and A ($\lambda$3) in the 480 portions to be measured (S1 to S480), and instead, information on the amount of received light A ($\lambda$1), A ($\lambda$2) and A ($\lambda$3) only in portions desired to be measured, for example, eight portions, needs to be collected. Therefore, only four light-transmitting probes 12T1 to 12T4 from among the 64 light-transmitting probes 12T1 to 12T64 and only four light-receiving probes 13R1 to 13R4 from among the 64 light-receiving probes 13R1 to 13R64 need to be attached. However, it still takes approximately one hour for the doctor or the other person to attach the holder 30 to the head of a subject, and then attach the light-transmitting probes 12T1 to 12T4 and the light-receiving probes 13R1 to 13R4 to the holder 30, though the subject only exercises for approximately one hour, such as for rehabilitation. That is to say, the time for preparation during which the subject puts the holder 30 and the light-transmitting probes 12T1 to 12T4 and the light-receiving probes 13R1 to 13R4 on the head is very long in comparison with the time during which the subject exercises, such as for rehabilitation.

Furthermore, some subjects exercise everyday, such as for rehabilitation, and in this case, the subject exercises at home, where it is very troublesome for his or her family to attach the holder 30 and the light-transmitting probes 12T1 to 12T4 and the light-receiving probes 13R1 to 13R4 to the head of the subject.

Means for Solving Problem

Research was carried out to find a holder that could be precisely put on the head of a subject in a short period of time, even when the subject is alone. When the above-described holder 30 is put on, it is necessary to push the hair aside in order for the ends of the light-transmitting probes $12_{T1}$ to $12_{T4}$ and the light-receiving probes $13_{R1}$ to $13_{R4}$ to make contact with the surface of the head. Therefore, the inventors have found a holder that can push the hair aside when the holder is put on the head. That is to say, a holder in comb shape has been provided.

When the above-described holder 30 is put on, a doctor or another person attaches the holder 30 to the head of a subject, and then attaches the light-transmitting probes $12_{T1}$ to $12_{T4}$ and the light-receiving probes $13_{R1}$ to $13_{R4}$ to the holder 30 in this order. The holder that can push the hair aside makes it possible to put the holder on the head of a subject after the light-transmitting probes $12_{T1}$ to $12_{T4}$ and the light-receiving probes $13_{R1}$ to $13_{R4}$ have been attached to the holder.

Accordingly, the extra task of pushing the hair aside is not necessary, and in addition, the attachment of the probes and the attachment of the holder can be carried out in this order, and therefore, a subject can put the holder and the light-transmitting probes $12_{T1}$ to $12_{T4}$ and the light-receiving probes $13_{R1}$ to $13_{R4}$ on his or her head, even when the subject is alone.

However, there is still a problem such that the subject by himself or herself cannot put the holder on his or her head in the precise location. As for the reference points set on the surface of the head of a human body, the International 10-20 system has been announced. Here, the International 10-20 system is described. FIG. 12 is a diagram for illustrating the International 10-20 system. In the International 10-20 system, first, an arrow-shaped center line is drawn to connect the nasion to the inion, and the arrow-shaped center line is divided into ten equal length sections. Here, the middle point of the arrow-shaped center line is referred to as vertex. In addition, a head circumference line is drawn from the nasion to the inion, passing through the point in front of the left ear lobe, and at the same time, a head circumference line is drawn from the nasion to the inion, passing through the point in front of the right ear lobe, and either head circumference line is divided into ten equal length sections. Next, four concentric circles of which the radius decreases by 1/10 of the arrow-shaped center line are drawn with the vertex as the center. Furthermore, sections for connecting each point that divides the head circumference line into ten equal length sections and the vertex are drawn, and thus, the coordinates according to the International 10-20 system are prepared.

Thus, the inventors have preset the first specific point as the vertex or Cz, for example, and found a holder where a disposition reference point is provided so as to match the vertex or Cz.

That is to say, the holder according to the present invention has at least two probe mount portions and is to be mounted on the head of a subject by inserting a light-transmitting probe for emitting light from the tip thereof or a light-receiving probe for receiving light from the tip thereof in a probe mount portion, and the holder is provided with: a linear backbone portion extending in a first direction; at least two linear branch portions extending in a second direction different from the above-described first direction; and a disposition reference point disposed so as to match a first specific point that is preset in the head of the above-described subject.

Here, "the first specific point" is any point that has been predetermined by the designer of the holder and is the vertex, an ear, the nasion or Cz according to the International 10-20 system that can be easily recognized, for example.

In addition, "the first direction" and "the second direction" are any directions that have been predetermined by the designer of the holder, and the second direction is the direction towards the front or towards the rear in which it is easy to insert the holder while pushing the hair aside, for example.

Furthermore, "the disposition reference point" may be indicated by anything visible or anything that can be recognized through the sense of touch, and a protrusion, a through hole or a mark can be cited as an example.

The holder according to the present invention is provided with a linear backbone portion extending in a first direction and at least two linear branch portions extending in a second direction. That is to say, the holder is in a comb shape. In addition, the holder according to the present invention is provided with a disposition reference point. Therefore, a subject puts the holder on his or her head by moving the holder in the second direction while pushing the hair aside so that the first specific point is made to match the disposition reference point while looking into a mirror or feeling with a finger.

Effects of the Invention

As described above, the holder according to the present invention can be precisely put on the head of a subject in a short period of time, even when the subject is alone.

(Other Means for Solving the Problem and Other Effects of the Invention)

In the holder according to the present invention, the above-described first specific point may be the vertex of the above-described subject or a point that indicates Cz according to the International 10-20 system, and the above-described disposition reference point may be indicated by a circular mark, a protrusion or a through hole.

The thus-made holder according to the present invention can be easily put on with precision.

In addition, a second specific point that is different from the first specific point may be preset on the head of the above-described subject, and the holder according to the present invention may be provided with a disposition reference line disposed along the line for connecting the above-described first specific point and second specific point.

Here, "the second specific point" is any point that has been predetermined by the designer of the holder and may be the vertex, an ear or the nasion that can be easily recognized, for example.

In addition, "the disposition reference line" may be indicated by anything visible or anything that can be recognized by the sense of touch, and a protrusion, a through hole or a mark can be cited as an example.

The thus-made holder according to the present invention can be easily put on with precision.

In addition, in the holder according to the present invention, the above-described second specific point may be a point indicating the nasion or an ear of the above-described subject, and the above-described disposition reference line may be a linear mark, a protrusion or a through hole.

In addition, in the holder according to the present invention, the above-described branch portions may be formed so as to be movable in the first direction and/or the second direction relative to the above-described backbone portion.

The holder according to the present invention can be used for an adult having a large head, an adult having a small head and a child instead of using a number of holders.

In addition, the light measuring device according to the present invention is provided with a holder as described above, a light-transmitting probe for emitting light to the above-described subject, a light-receiving probe for receiving light emitted from the above-described subject, and a control unit for gaming measurement data concerning the brain activity of the above-described subject by controlling the above-described light-transmitting probe and light-receiving probe.

BEST MODE FOR CARRYING OUT THE INVENTION

In the following, the preferred embodiments of the present invention are described in reference to the drawings. Here, the present invention is not limited to the below-described embodiments and naturally includes various modifications as long as the gist of the present invention is not deviated from.

First Embodiment

Figure 1:
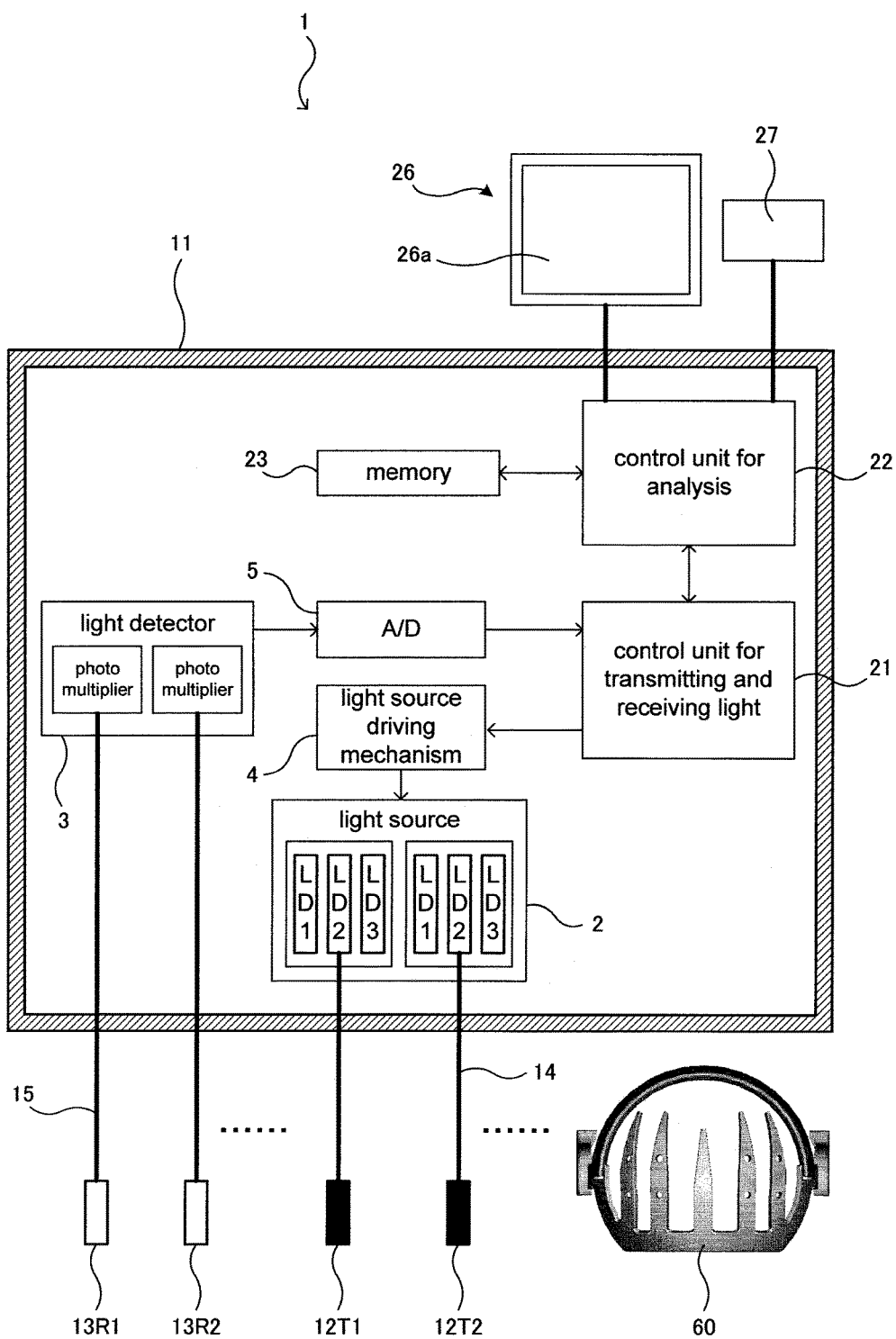
FIG. 1 is a block diagram schematically showing the structure of the light measuring device according to one embodiment of the present invention.
Figure 2:
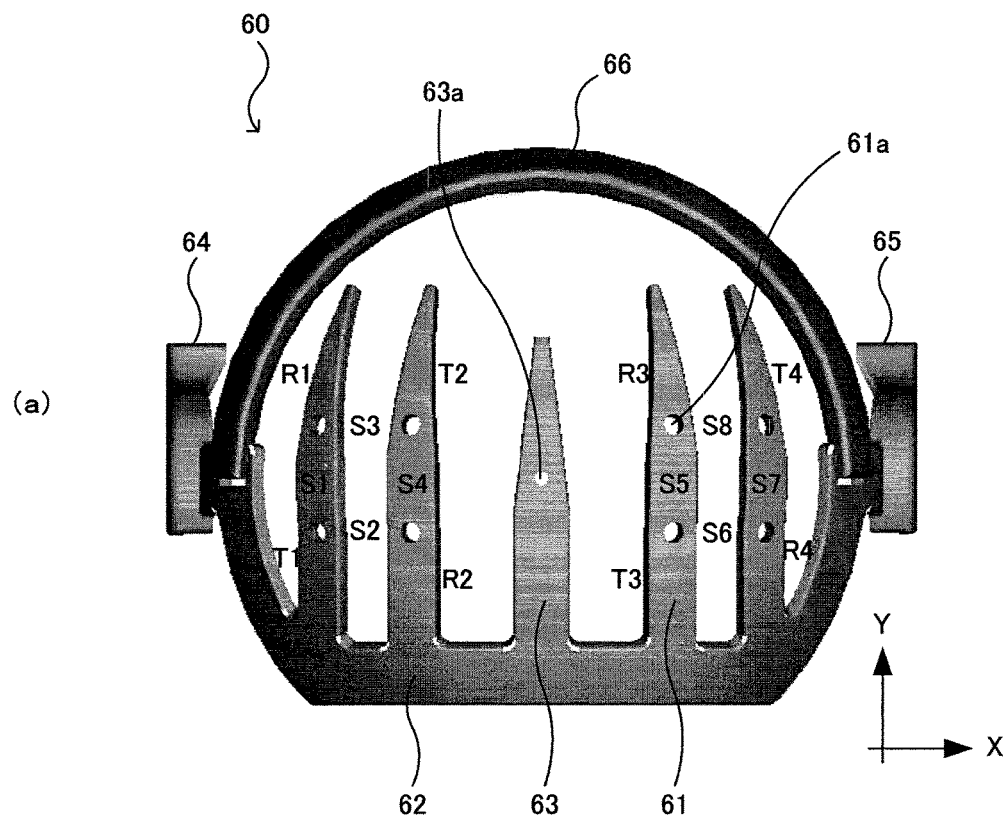
FIGS. 2(a) and 2(b) are diagrams showing an example of the holder.
Figure 2:
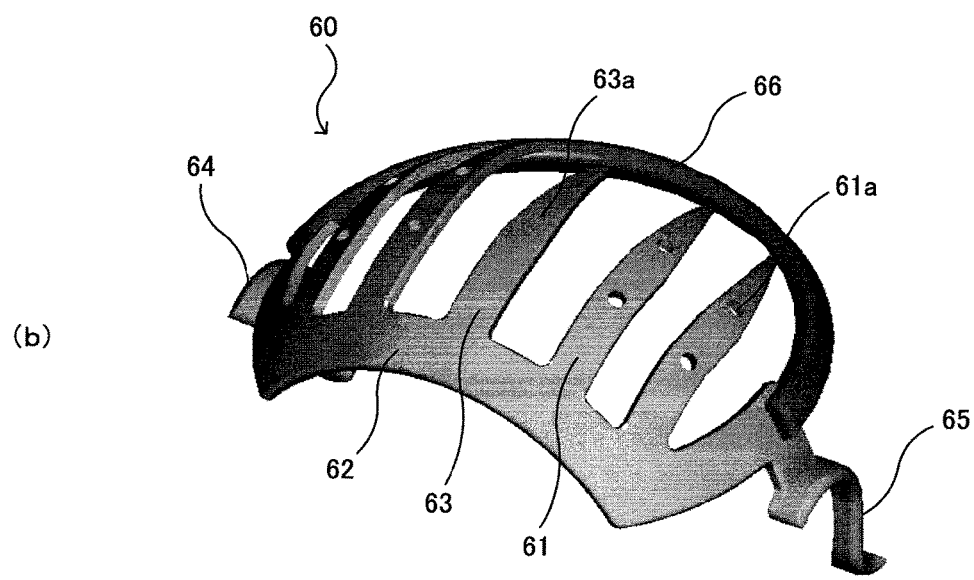

FIG. 1 is a block diagram schematically showing the structure of the light measuring device according to one embodiment of the present invention. FIGS. 2(a) and 2(b) are diagrams showing an example of the holder. Here, the same symbols are attached to the same components as in the near infrared spectrometer 201. The light measuring device 1 is to be used in a hospital.

The light measuring device 1 has a housing 11 in rectangular parallelepiped form (70 cm×100 cm×120 cm, for example).

A light source 2 for emitting light, a light source driving mechanism 4 for driving the light source 2, a light detector 3 for detecting light, an A/D converter 5, a control unit for transmitting and receiving light 21, a control unit for analysis 22 and a memory 23 are provided inside the housing 11, and at the same time, 64 light-transmitting probes (light-transmitting means) 12, 64 light-receiving probes (light-receiving means) 13, 64 optical fibers 14 for transmitting light, 64 optical fibers 15 for receiving light, a display 26 having a monitor screen 26a, and a keyboard (input device) 27 are provided with the outside of the housing 11.

A holder 60 is described below. FIG. 2(a) is a plan diagram showing a holder, and FIG. 2(b) is a perspective diagram showing the holder in FIG. 2(a).

The holder 60 is provided with one linear backbone portion 62, four linear first branch portions 61, one linear second branch portion 63, a right end portion 64 that hooks onto the right ear, a left end portion 65 that hooks onto the left ear, and a band 66 for fixing the holder 60 onto the head.

The backbone portion 62 extends in the direction X (first direction) as viewed from above and is in arc form as viewed from the front. The backbone portion 62 has a width of 15 mm, a thickness of 0.1 mm and a length of 120 mm, for example.

The second branch portion 63 extends in the direction Y (second direction) that is perpendicular to the direction X and has a width of 15 mm, a thickness of 0.1 mm and a length of 60 mm. In addition, a first end of the second branch portion 63 is connected to the center portion of the backbone portion 62. A second end of the second branch portion 63 is tapered in order to push the hair aside.

Furthermore, a disposition reference point 63a is defined as a circular through hole (diameter: 7 mm, for example) in a location 45 mm away from the first end of the second branch portion 63 towards the second end.

Here, it has been preset for the holder 60 that the first specific point is the vertex, and thus, the disposition reference point 63a matches the vertex when the holder 60 is put on the head. In addition, the second branch 63 matches the line for connecting the vertex and the nasion when the holder 60 is put on the head.

The first branch portions 61 extend in the direction Y (second direction) that is perpendicular to the direction X and have a width of 15 mm, a thickness of 0.1 mm and a length of 90 mm, for example. First ends of two first branch portions 61 are connected to locations 30 mm and 61.5 mm away from the center portion of the backbone portion 62 towards the right, and at the same time, first ends of the other two first branch portions 61 are connected to locations 30 mm and 61.5 mm away from the center portion of the backbone portion 62 towards the left. Second ends of the first branch portions 61 are tapered in order to push the hair aside.

Furthermore, circular through holes (probe mount portions with a diameter of 7 mm) 61a are created in the locations 30 mm and 61.5 mm away from the first end of each first branch portion 61 towards the second end. As a result, the through holes 61a form squares with sides of 31.5 mm on the left and right of the disposition reference point 63a.

It is possible to insert a light-transmitting probe 12 or a light-receiving probe 13 into the through holes 61a. Thus, a total of eight pieces (S1 to S8) of information on the amount of received light A ($\lambda_1$), A ($\lambda_2$) and A ($\lambda_3$) can be collected as shown in FIG. 2(a) as a plan view when light-transmitting probes $12_{T1}$ to $12_{T4}$ and light-receiving probes $13_{R1}$ to $13_{R4}$ are inserted into the through holes 61a with the corresponding numbers.

The right end portion 64 is connected to the left end of the backbone portion 62 and can hook onto the right ear. In addition, the left end portion 65 is connected to the right end of the backbone portion 62 and can hook onto the left ear.

The material for forming the backbone portion 62, the first branch portions 61, the second branch portions 63, the right end portion 64 and the left end portion 65 is not particularly limited, but polypropylene, polyvinyl chloride, polyacetal and metals can be cited as examples.

The band 66 is formed so as to connect the right end and the left end of the backbone portion 62.

The material for forming this band 66 is not particularly limited, but rubber having stretchability can be cited as an example.

In the thus-formed light measuring device 1, first, a subject inserts the light-transmitting probes $12_{T1}$ to $12_{T4}$ and the light-receiving probes $13_{R1}$ to $13_{R4}$ into the through holes 61a of the holder 60 in a predetermined alignment. That is to say, the subject himself or herself can attach the light-transmitting probes $12_{T1}$ to $12_{T4}$ and the light-receiving probes $13_{R1}$ to $13_{R4}$ to the through holes 61a of the holder 60.

Next, the subject puts the holder 60 on the head in such a manner that the holder 60 pushes the hair aside when moved from the front towards the rear of the head.

Thus, the subject, while looking into a mirror or the like, adjusts the position of the holder so that the disposition reference point 63a matches the vertex, and at the same time, the second branch portion 63 matches the line for connecting the vertex and the nasion.

Furthermore, the holder 60 is fixed onto the head with the right end portion 64, the left end portion 65 and the band 86.

As described above, in the light measuring system 1 according to the present invention, a subject by himself or herself can precisely put the holder 60 on his or her own head in a short period of time.

Second Embodiment

Figure 3:
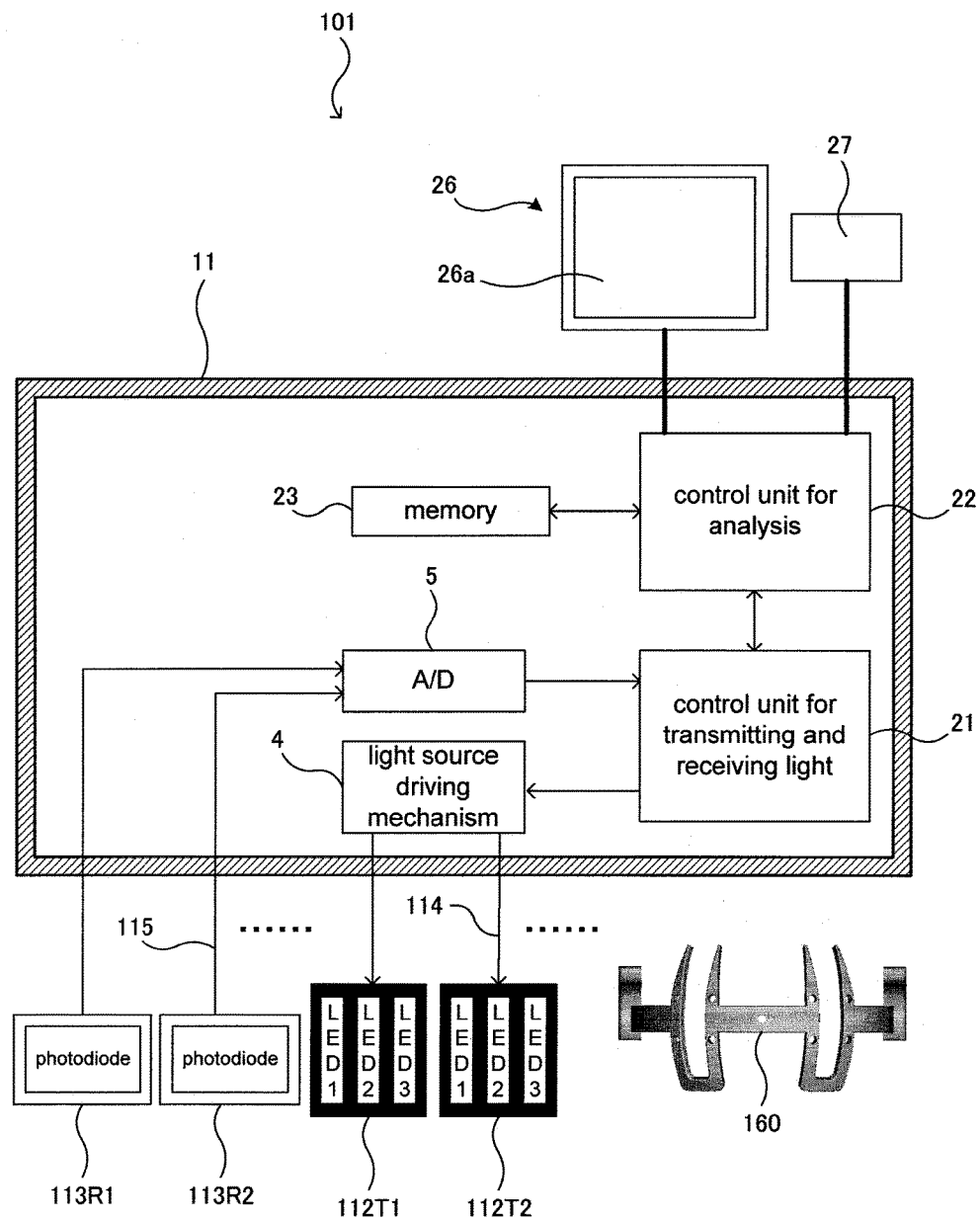
FIG. 3 is a block diagram schematically showing the structure of the light measuring device according to another embodiment of the present invention.
Figure 4:
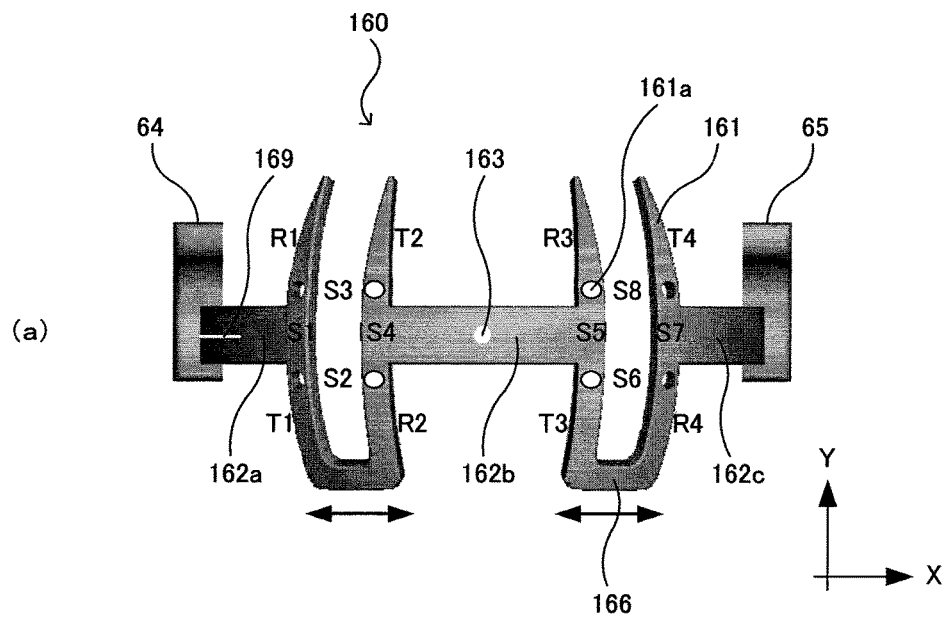
FIGS. 4(a) and 4(b) are diagrams showing another example of the holder.
Figure 4:
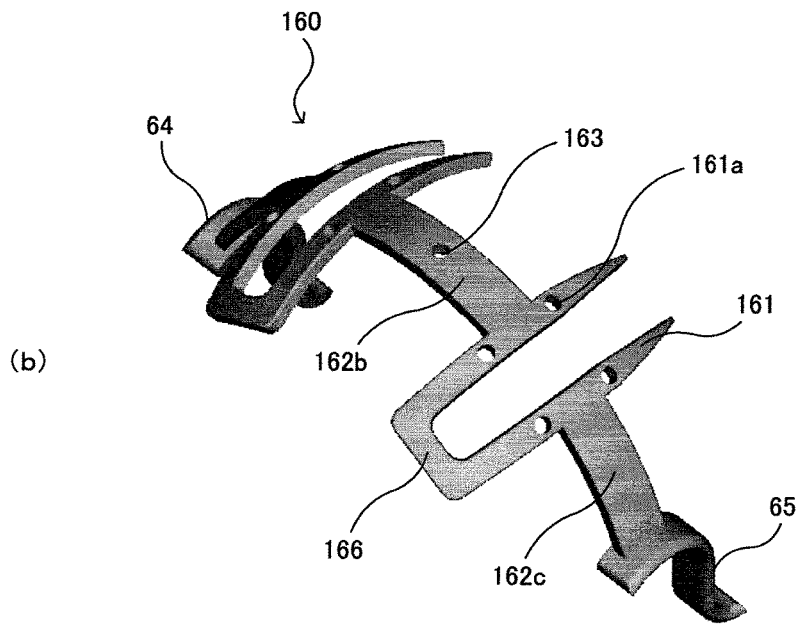

FIG. 3 is a block diagram schematically showing the structure of the light measuring device according to another embodiment of the present invention. FIGS. 4(a) and 4(b) are diagrams showing another example of the holder. The same symbols are attached to the same components as in the light measuring device 1. In addition, the light measuring device 101 is to be used at a subject's home.

The light measuring device 101 has a housing 11 in rectangular parallelepiped form (70 cm×100 cm×120 cm, for example).

A light source driving mechanism 4 for driving the light source, an A/D converter 5, a control unit 21 for transmitting and receiving light, a control unit 22 for analysis and a memory 23 are provided inside the housing 11, and at the same time, four light-transmitting probes (light-transmitting means) 112, four light-receiving probes (light-receiving means) 113, four electrical wires 114, four electrical wires 115, a display 28 having a monitor screen 28a, and a keyboard (input device) 27 are provided outside the housing 11.

Figure 6:
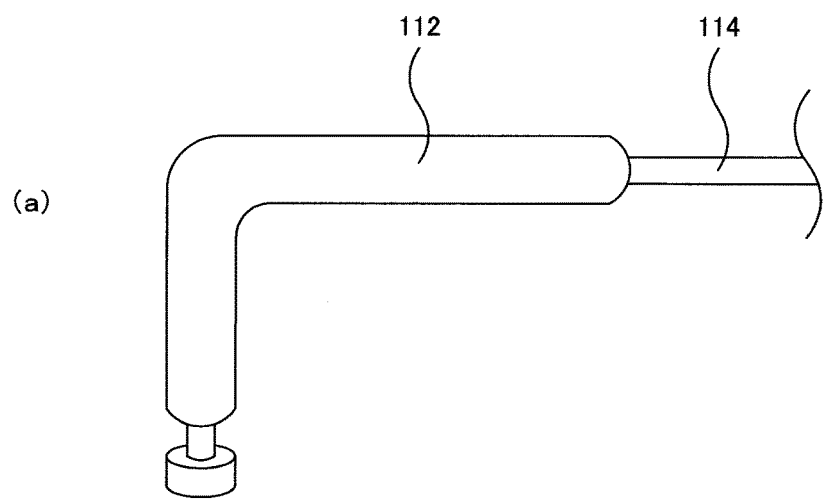
FIGS. 6(a) and 6(b) are diagrams showing an example of a light-transmitting probe.
Figure 6:
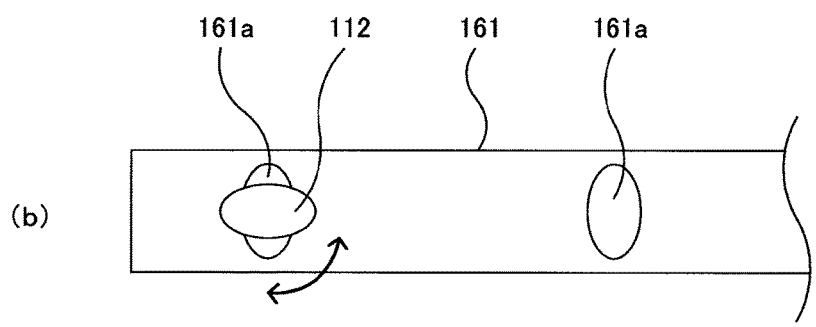
Figure 7:
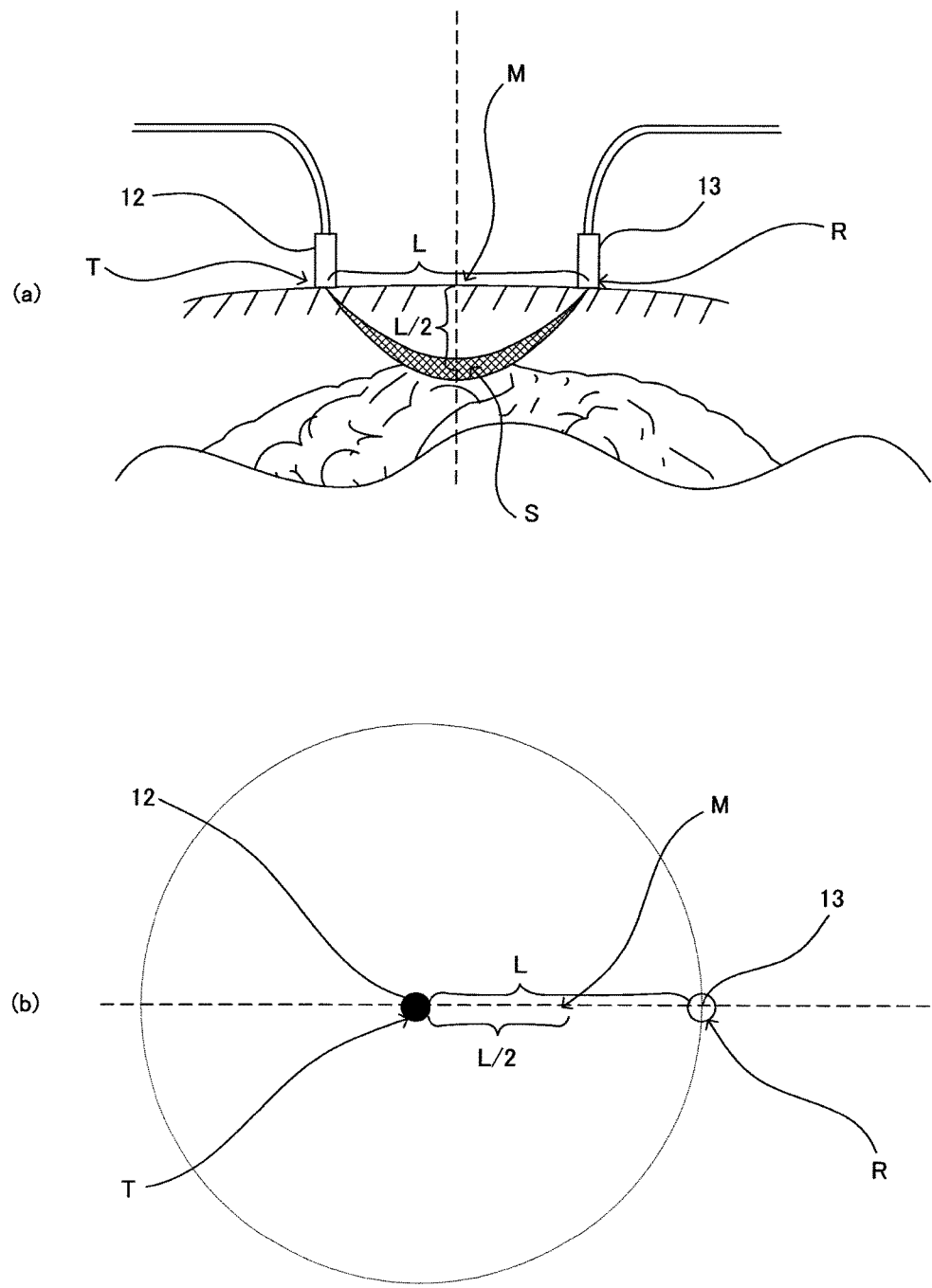
FIGS. 7(a) and 7(b) are diagrams showing the relationship between a pair of probes, a light-transmitting probe and a light-receiving probe, and a portion to be measured.
Figure 8:
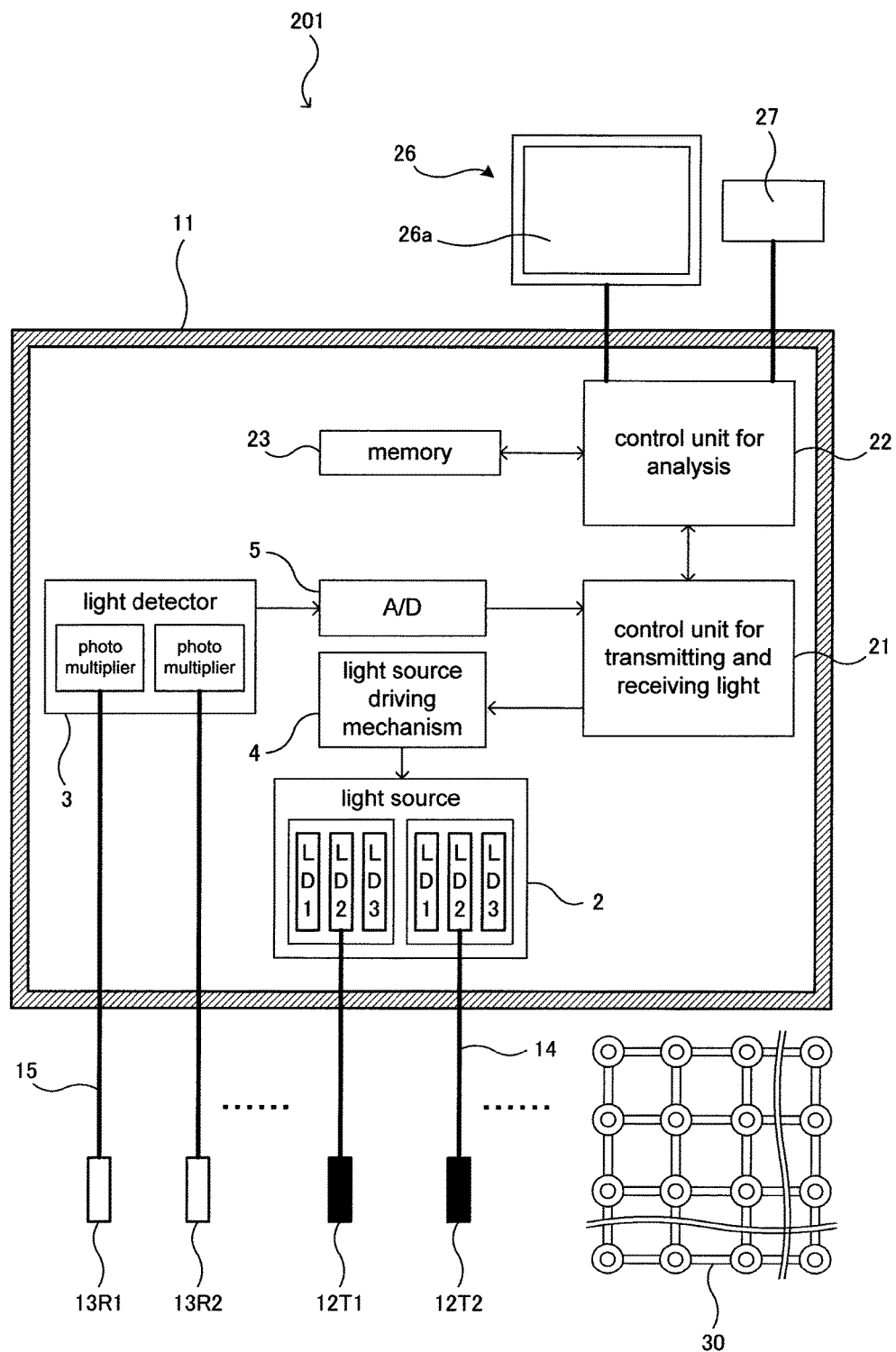
FIG. 8 is a block diagram schematically showing an example of the structure of a conventional near infrared spectrometer.
Figure 9:
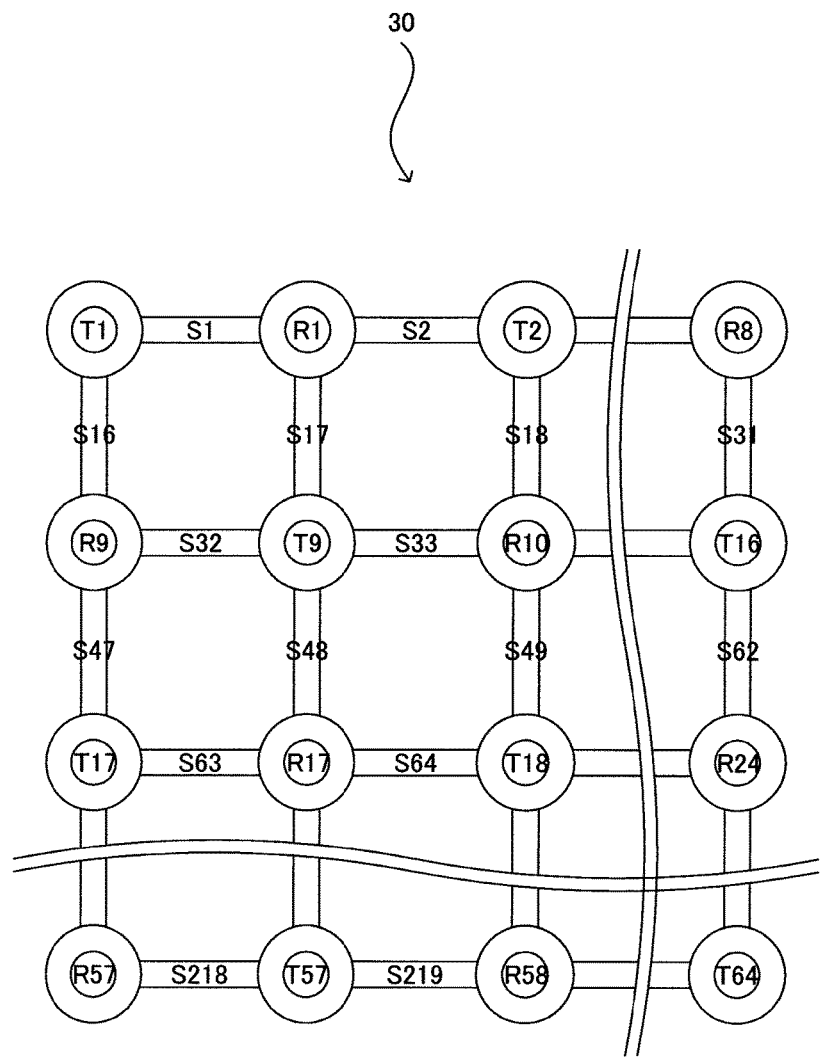
FIG. 9 is a plan diagram showing an example of a holder.
Figure 10:
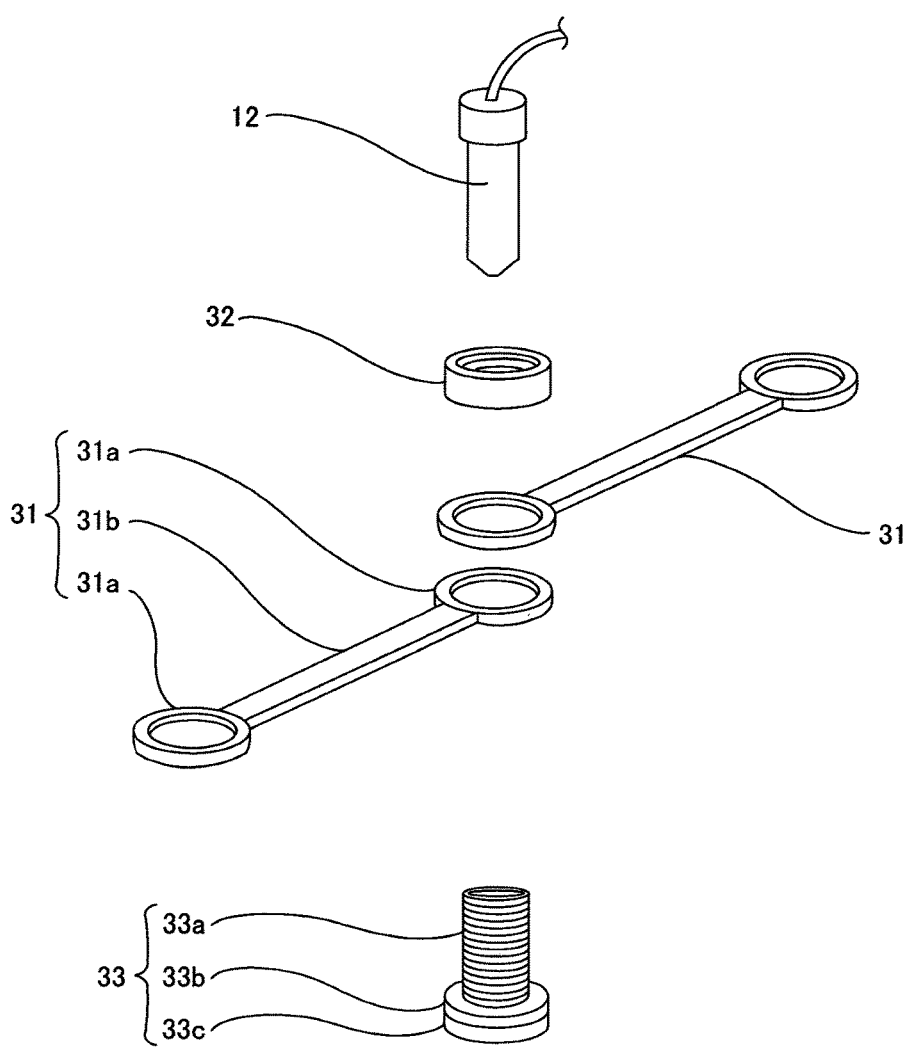
FIG. 10 is an exploded perspective diagram showing a light-transmitting probe, a nut part, two connection parts and a socket part.
Figure 11:
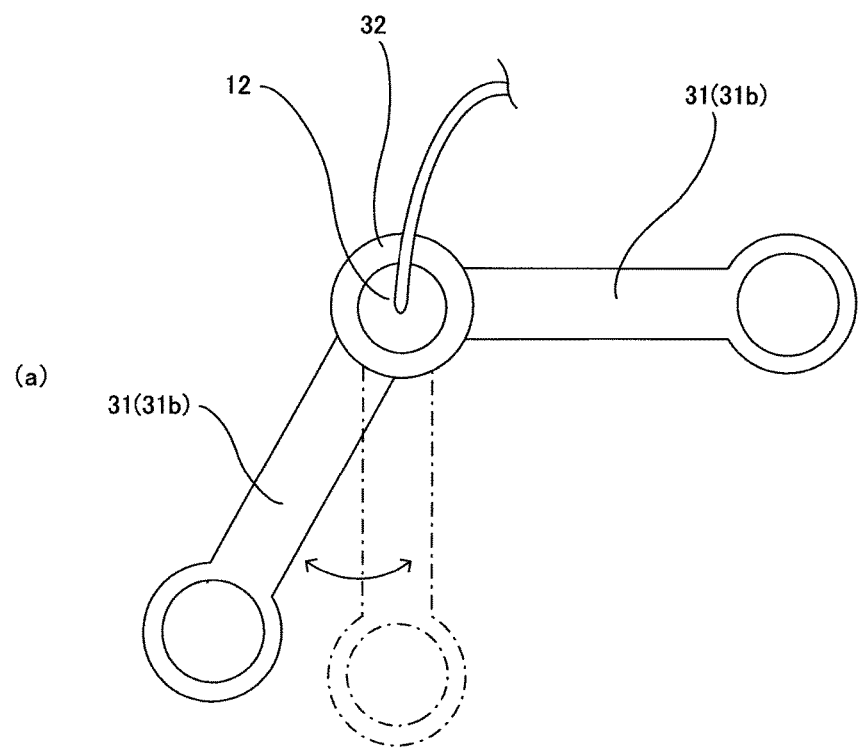
FIGS. 11(a) and 11(b) are diagrams showing the light-transmitting probe, the nut part, the two connection parts and the socket part after assembly.
Figure 11:
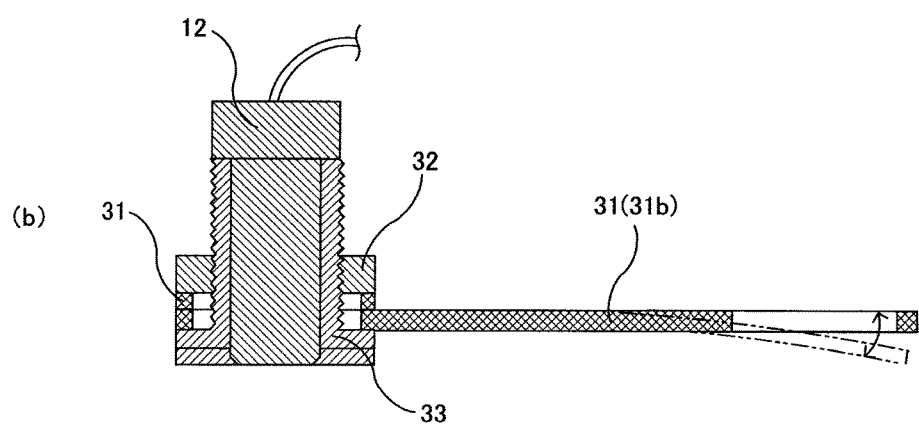
Figure 12:
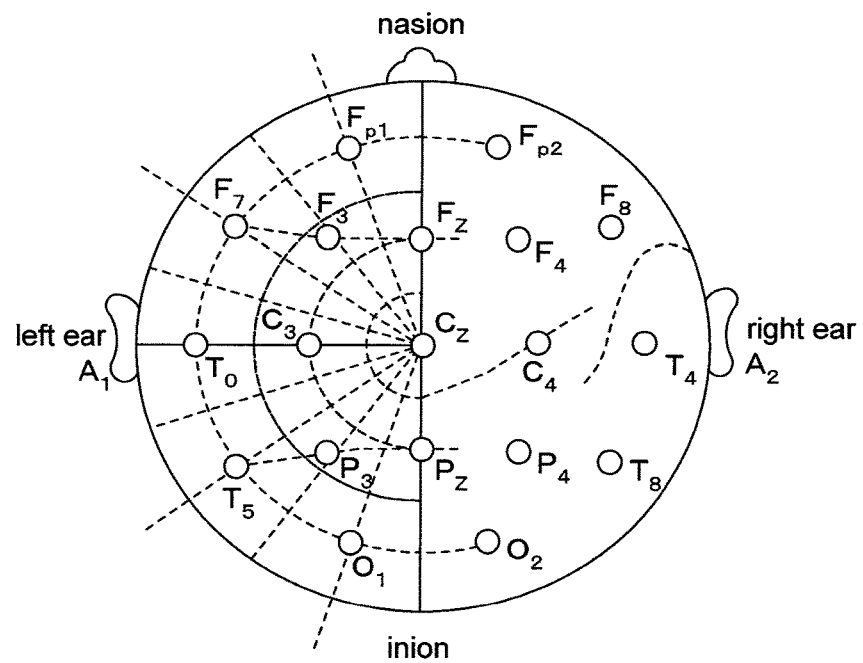
FIG. 12 is a diagram for illustrating the International 10-20 system.
Figure 12:
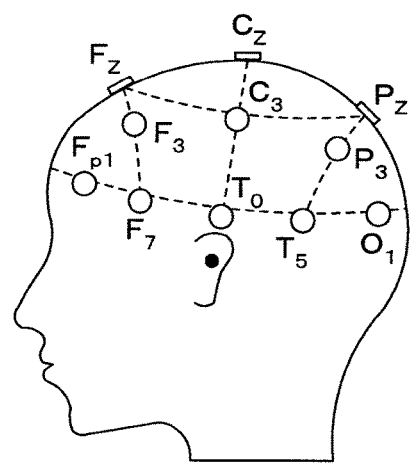

The tip portion of the light-transmitting probes 112 is in an elliptical columnar form having a recess that makes it possible to secure the tip portion to the holder 160 (see FIG. 6(a)). In addition, a light source is fixed inside the light-transmitting probes 112 so that light can be emitted from the tip of the light-transmitting probes 112. The light source includes light-emitting diodes LED1, LED2, LED3 and the like that can emit near infrared rays having three different wavelengths $\lambda_1$, $\lambda_2$ and $\lambda_3$, for example.

In addition, the tip portion of the light-receiving probes 113 is in an elliptical columnar form having a recess that makes it possible to secure the tip portion to the holder 160. In addition, a light detector is fixed inside the light-receiving probes 113 so that light can be received by the tip of the light-receiving probes 113. The light detectors are detectors for outputting a light reception signal (information on the amount of received light) A ($\lambda_1$), A ($\lambda_2$) and A ($\lambda_3$) to the control unit 21 for transmitting and receiving light through the A/D converter 5, and an example of these is a photodiode.

The holder 160 is described below. FIG. 4(a) is a plan diagram showing the holder, and FIG. 4(b) is a perspective diagram showing the holder in FIG. 4(a).

The holder 160 is provided with a linear backbone portion 162, four linear first branch portions 161, two linking portions 168, a right end portion 64 that hooks onto the right ear, and a left end portion 65 that hooks onto the left ear.

The backbone portion 162 is divided into three pieces: a right side portion 162a, a center portion 162b and a left side portion 162c, and extends in the direction X (first direction) so as to be in an arc form as viewed from the front with spaces between the right side portion 162a and the center portion 162b as well as between the center portion 162b and the left side portion 162c. In addition, the right side portion 162a, the center portion 162b and the left side portion 162c have a width of 15 mm and a thickness of 0.1 mm, for example.

A disposition reference point 163 is defined as a circular through hole (diameter: 7 mm, for example) at the center of the center portion 162b. In addition, a disposition reference line 169 is defined as a linear mark extending in the direction X in the right side portion 162a.

Here, it has been preset for the holder 160 that a first specific point is the vertex, and thus, the disposition reference point 163 matches the vertex when the holder 160 is put on the head. In addition, the disposition reference line 169 matches the line for connecting the vertex and the right ear when the holder 160 is put on the head.

The first branch portions 161 extend in the direction Y (second direction) that is perpendicular to the direction X and have a width of 15 mm, a thickness of 0.1 mm and a length of 90 mm, for example. Furthermore, through holes (probe mount portions) 161a in elliptical form that is long in the direction X are created in the locations 30 mm and 61.5 mm away from first ends of the first branch portions 161 towards second ends.

In addition, a linking portion 163 is formed so as to link the first end of the first branch portion 161 to the first end of the second first branch portion 161 with a distance of 31.5 mm in the direction X between them. That is to say, a first U-shaped, body is formed. As a result, the through holes 161a form a first square with sides of 31.5 mm.

Furthermore, a linking portion 163 is formed so as to link the first end of the third first branch portion 161 to the first end of the fourth first branch portion 161 with a distance of 31.5 mm in the direction X between them. That is to say, a second U-shaped body is formed. As a result, the through holes 161a form a second square with sides of 31.5 mm.

It is possible to insert a light-transmitting probe 112 or a light-receiving probe 113 into the through holes 161a so as to be fixed (see FIG. 6(b)). Thus, a total of eight pieces (S1 to S8) of information on the amount of received light A ($\lambda_1$), A ($\lambda_2$) and A ($\lambda_3$) can be collected as shown in FIG. 4(a) as a plan view when light-transmitting probes $112_{T1}$ to $112_{T4}$ and light-receiving probes $113_{R1}$ to $113_{R4}$ are inserted into the through holes 161a with the corresponding numbers.

In addition, the second ends of the first branch portions 161 are tapered in order to push the hair aside.

The left side portion 162a is connected to the left side of the first branch portion 161 at the center in the first U-shaped body, and at the same time, an insertion plate 167 that extends by a predetermined distance to the right is formed on the right side of the second first branch portion 161 at the center. Meanwhile, an insertion hole 162d that extends by a predetermined distance to the right is created on the left side of the center portion 162b (see FIGS. 5(a) and 5(b)). Here, the surfaces of the insertion plate 167 and the insertion hole 162d have been processed so as to be rugged.

Figure 5:
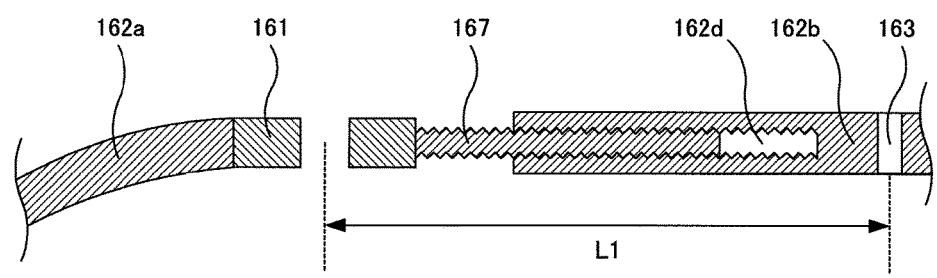
FIGS. 5(a) and 5(b) are diagrams showing an example of the holder.
Figure 5:
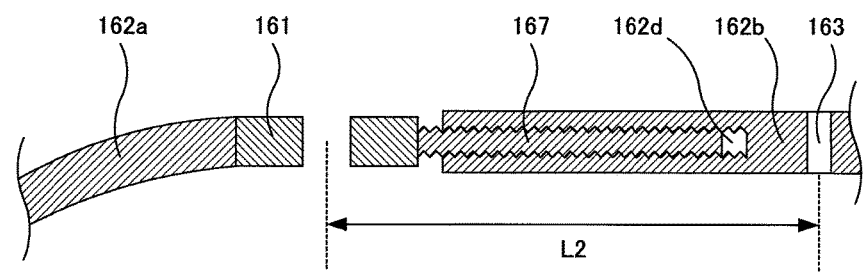

As a result, as shown in FIGS. 5(a) and 5(b), the insertion plate 167 can be inserted into the insertion hole 162d so that the insertion hole 162d and the insertion plate 167 can be engaged over a distance L1 or L2. That is to say, the first U-shaped body is movable in the direction X relative to the center portion 162b.

In addition, the right side portion 162c is connected to the right side of the fourth first branch portion 161 at the center in the second U-shaped body, and at the same time, an insertion plate (not shown) that extends by a predetermined distance to the left is formed on the left side of the third first branch portion 161 at the center. Meanwhile, an insertion hole (not shown) that extends by a predetermined distance to the left is created on the right side of the center portion 162b. Here, the surfaces of the insertion plate and the insertion hole have been processed so as to be rugged.

As a result, the insertion plate can be inserted into the insertion hole so that the insertion hole and the insertion plate can be engaged over a desired distance. That is to say, the second U-shaped body is movable in the direction X relative to the center portion 162b.

In the thus-formed light measuring device 101, first, a subject inserts the light-transmitting probes $112_{T1}$ to $112_{T4}$ and the light-receiving probes $113_{R1}$ to $113_{R4}$ into the through holes 161a of the holder 160 in a predetermined alignment. That is to say, the subject himself or herself can attach the light-transmitting probes $112_{T1}$ to $112_{T4}$ and the light-receiving probes $113_{R1}$ to $113_{R4}$ to the through holes 161a of the holder 160.

Next, the subject puts the holder 160 on the head in such a manner that the holder 160 pushes the hair aside when moved from the front towards the rear of the head.

Thus, the subject, while checking the positions of the disposition reference point 163 and the disposition reference line 169 with his or her fingers, adjusts the position of the holder so that the disposition reference point 163 matches the vertex, and at the same time, the disposition reference line 169 matches the line for connecting the vertex and the right ear.

Furthermore, the holder 160 is fixed onto the head with the right end portion 64 and the left end portion 65.

As described above, in the light measuring device 101 according to the present invention, a subject by himself or herself can precisely put the holder 160 on his or her own head in a short period of time. In addition, the holder 160 can be used for an adult having a large head an adult having a small head and a child.

Other Embodiments (1) Though in the above-described light measuring device 1 the structure allows the holder 60 to be put on the head when being moved from the front towards the rear of the head, the structure may allow the holder to be put on the head when being moved from the right side towards the left side of the head.

(2) Though in the above-described light measuring device 1 the structure allows four light-transmitting probes $12_{T1}$ to $12_{T4}$ and four light-receiving probes $13_{R1}$ to $13_{R4}$ to be attached to the holder 60, the structure may allow eight light-transmitting probes and eight light-receiving probes to be attached to the holder or may allow two light-transmitting probes and two light-receiving probes to be attached to the holder.

(3) Though in the above-described light measuring device 101 the structure allows the first U-shaped body and the second U-shaped body to be movable in the direction X relative to the center portion 162b, the structure may allow the first U-shaped body and the second U-shaped body to be movable in the direction Y.

INDUSTRIAL APPLICABILITY

The present invention can be applied to a light measuring device for acquiring information on the inside of a living body by irradiating the inside of the living body with light.

EXPLANATION OF SYMBOLS

1: light measuring device
11: housing
12: light-transmitting probe (light-transmitting means)
13: light-receiving probe (light-receiving means)
14: optical fiber for transmitting light
15: optical fiber for receiving light
22: control unit for analysis
26: display
27: keyboard (input device)
60: holder
61: branch portion
61a: through hole (probe mount portion)
62: backbone portion
63a: disposition reference point

The invention claimed is:

1. A holder configured to be mounted on the head of a subject, comprising:
    a linear backbone portion extending in a first direction;
    at least two linear branch portions, extending from the linear backbone portion along a second direction from a front of the head toward a back of the head when the holder is adapted to be mounted on the head of the subject, each configured to hold at least one of a light-transmitting probe for emitting light and a light-receiving probe for receiving light, free ends of the at least two linear branch portions being tapered to comb hair of the subject when the holder is adapted to be mounted on the head of the subject to cause the tapered free ends to be adapted to be inserted into the hair of the subject along the second direction; and
    a disposition reference point disposed so as to match a first specific point that is preset on the head of said subject.

2. The holder according to claim 1, wherein
    said first specific point is the vertex of said subject or the point showing Cz in the International 10-20 system, and
    said disposition reference point is indicated by a circular mark, a protrusion or a through hole.

3. The holder according to claim 1, wherein a second specific point that is different from the first specific point is preset on the head of said subject, and the holder further comprises a disposition reference line disposed along the line for connecting said first specific point and said second specific point.

4. The holder according to claim 1, wherein
    said second specific point is a point indicating the nasion or an ear of said subject, and said disposition reference line is indicated by a linear mark, a protrusion or a through hole.

5. The holder according to claim 1, wherein said branches are formed so as to be movable in the first direction and/or the second direction relative to said backbone portion.

6. A light measuring device comprising:
the holder according to claim 1;
a light-transmitting probe for emitting light to said subject;
a light-receiving probe for receiving light emitted from said subject; and
a control unit for acquiring measurement data concerning the brain activity of said subject by controlling said light-transmitting probe and said light-receiving probe.

* * * * *